(12) United States Patent
Glausch et al.

(10) Patent No.: US 6,176,918 B1
(45) Date of Patent: Jan. 23, 2001

(54) MODIFIED NACREOUS LUSTER PIGMENTS FOR WATER PAINT SYSTEMS

(75) Inventors: Ralf Glausch; Nicole Fornoff, both of Darmstadt; Joachim Duschek, Pfungstadt; Burkhard Standke, Lörrach; Roland Edelmann, Wehr, all of (DE)

(73) Assignee: Merck Patent Gesellschaft mit Beschrankter Haftung and Huels AG (DE)

( * ) Notice: Under 35 U.S.C. 154(b), the term of this patent shall be extended for 0 days.

(21) Appl. No.: 09/077,121

(22) PCT Filed: Sep. 12, 1997

(86) PCT No.: PCT/EP97/04999

§ 371 Date: May 22, 1998

§ 102(e) Date: May 22, 1998

(87) PCT Pub. No.: WO98/13426

PCT Pub. Date: Apr. 2, 1998

(30) Foreign Application Priority Data

Sep. 27, 1996 (DE) .............................. 196 39 783

(51) Int. Cl.[7] .................. C09C 1/00; C09C 3/12; C09D 7/12; C08K 9/06; A61K 7/00
(52) U.S. Cl. .................. 106/415; 106/416; 106/417; 106/436; 106/438; 106/439; 106/442; 106/445; 106/446; 106/447; 106/448; 106/450; 106/455; 106/460; 106/481; 106/482; 106/483; 106/490
(58) Field of Search ................ 106/415, 416, 106/417, 436, 438, 439, 442, 445, 446, 447, 448, 450, 459, 460, 481, 482, 483, 490

(56) References Cited

U.S. PATENT DOCUMENTS

| | | | |
|---|---|---|---|
| 4,828,623 | * | 5/1989 | Nitta et al. .............................. 106/450 |
| 5,223,034 | * | 6/1993 | Nitta et al. .............................. 106/417 |
| 5,356,471 | * | 10/1994 | Reynders ................................ 106/489 |
| 5,472,491 | * | 12/1995 | Duschek et al. ...................... 106/418 |
| 5,540,770 | * | 7/1996 | Schmid et al. ........................ 106/415 |
| 5,629,400 | * | 5/1997 | Standke et al. ........................ 528/38 |
| 5,679,147 | * | 10/1997 | Standke et al. ................. 106/287.11 |
| 5,759,255 | * | 6/1998 | Venturini et al. ..................... 106/418 |
| 5,766,335 | * | 6/1998 | Bujard et al. ......................... 106/404 |
| 5,873,934 | * | 2/1999 | Kunii et al. ............................ 106/417 |

FOREIGN PATENT DOCUMENTS

| | | | | |
|---|---|---|---|---|
| 2723871 | * | 12/1977 | (DE) .................................... 106/418 |
| 3235017 | * | 3/1984 | (DE) .................................... 106/418 |
| 4313541 | * | 10/1994 | (DE) .................................... 106/418 |
| 675 128 | * | 10/1995 | (EP) . | |

OTHER PUBLICATIONS

Product Information Sheet, "Research–Development–Application Silanes "Dynasylan HS"", Sivento Research Labs [No Date].*

* cited by examiner

Primary Examiner—Anthony Green
(74) Attorney, Agent, or Firm—Millen, White, Zelano, & Branigan, P.C.

(57) ABSTRACT

Modified pearl luster pigments for waterborn coating systems, based on a platelet-form substrate coated with metal oxides and, located on the topmost metal oxide layer, a top layer consisting of at least two oxides and/or mixed oxides from the group consisting of silicon dioxide, aluminium oxide, cerium oxide, titanium oxide and zirconium oxide, and on a water-based oligomeric silane system. The oligomeric silane system can be described, for example, by the following approximate structure:

$$[HO[Si(A)(OH)_z(CH_3)_{1-z}O]_a[Si(B)(OH)_y(CH_3)_{1-y}O]_b[Si(E)(O-H)_w(CH_3)_{1-w}O]_c[Si(D)(OH)_v(CH_3)_{1-v}O]_dH]\cdot(HX)_e \quad (IX)$$

where
A=aminoalkyl radical derived from the general formula V,
B=glycidyl ether alkyl radical derived from the general formula VI,
E=acryloxyalkyl or methacryloxyalkyl radical of the general formula VII,
D=alkyl radical of the general formula VIII,
HX=monobasic acid, where X=inorganic or organic acid radical such as, for example, chloride, nitrate, formate, acetate,
v is equal to 0 or 1 and w is equal to 0 or 1 and y is equal to 0 or 1 and z is equal to 0 or 1 and $a+b+c+d \geq 4$ and $a \leq e \leq 2a$, where $0 \leq a/(b+c+d) \leq 3$, especially for $a/(b+c+d)$ equal to 0 if a=0 and/or c equal to d equal to 0 and $b \geq 1$ and also for $0.5 \leq a/(b+c+d) \leq 3$.

14 Claims, No Drawings

MODIFIED NACREOUS LUSTER PIGMENTS FOR WATER PAINT SYSTEMS

The invention relates to surface-modified pearl lustre pigments for waterborne coating systems.

BACKGROUND OF THE INVENTION

It is known that titanium dioxide particles present as the pigment component in a coating material cause oxidative decomposition of the polymer on exposure to ultraviolet rays and moisture, which is known as whitening. In order to suppress this effect of titanium dioxide, it has been proposed to coat or dope titanium dioxide with compounds of chromium, silicon, aluminium, zinc, phosphorus or zirconium.

EP-A-0 268 918 describes a weathering-resistant pearl lustre pigment having a hydrated zirconium oxide coating on the titanium dioxide base pigment, this coating being obtained by hydrolysis of a zirconium salt in the presence of a hypophosphite.

EP-A-0 342 533 describes a weathering-resistant pearl lustre pigment having, on the titanium dioxide base pigment, a top layer which consists of hydrated zirconium oxide, obtained by hydrolysis in the presence of a hypophosphite, and a hydrated metal oxide. The metal oxide can be cobalt oxide, manganese oxide or cerium oxide.

The modified pearl lustre pigments possess sufficient dispersibility and weathering resistance in nonaqueous coating systems. However, they are unsuitable for use in water-thinable coating systems, since they cause the formation of microfine bubbles in the coating film which significantly increase light scattering and thus have an adverse effect on lustre and colour. In addition, the distinctness of image (DOI) is severely reduced and the regeneration capacity of the coating film is impaired.

U.S. Pat. No. 5,472,491 describes a pearl lustre pigment based on a platelet-form substrate coated with metal oxides and on a top layer which is located on the metal oxide layer and consists of silicon dioxide, at least one further metal hydroxide or metal hydrate of the elements cerium, aluminium or zirconium, and at least one organic coupling reagent. This coupling reagent can be a zirconium aluminate, a metal-acid ester or an organofunctional silane. The coupling reagents must be hydrolysed before binding to the pigment surface. When two or more compounds are used, problems occur as a result of different rates of hydrolysis. Moreover, not more than 60% of the coupling reagents added can be bound to the pigment surface, as a result of which it is necessary to make a corresponding increase in the material employed. The non-coupled fractions remain in the reaction medium and impair the filterability of the pigment. For the binding of the pigment to the coating binder, however, it is necessary for different functional groups to be present on the pigment surface.

SUMMARY OF THE INVENTION

It is therefore an object of the present invention to provide a pearl lustre pigment having an aftercoat which contains coupling reagents by means of which the disadvantages of the aftercoat described in U.S. Pat. No. 5,472,491 are avoided.

This object is achieved in accordance with the present invention by a pearl lustre pigment based on a platelet-form substrate coated with metal oxides and on a top layer which is located on the metal oxide layer and consists of at least two oxides and/or mixed oxides from the group consisting of silicon dioxide, aluminium oxide, cerium oxide, titanium oxide and zirconium oxide, and consists of a water-based oligomeric silane system.

The water-based oligomeric silane system is known from EP 0 675 128, EP 0 716 127 and EP 0 716 128. It is prepared by Mixing water-soluble aminoalkylalkoxysilanes of the general formula I

$$R\!-\!Si(R^1)_v(OR^{1*})_{3-v} \qquad (I),$$

preferably aminopropyltriethoxysilane, aminopropylmethyldiethoxysilane, aminopropyltrimethoxysilane or aminopropylmethyldimethoxysilane, with water-insoluble alkyltrialkoxysilanes of the general formula IIa

$$R^2\!-\!Si(OR^{1**})_3 \qquad (IIa),$$

preferably propyltrimethoxysilane, propyltriethoxysilane, methyltriethoxysilane, methyltrimethoxysilane, ethyltrimethoxysilane, ethyltriethoxysilane, isobutyltrimethoxysilane or isobutyltriethoxysilane, and/or water-insoluble dialkyldialkoxysilanes of the general formula III

$$AA'\!-\!Si(OR^{1***})_2 \qquad (III),$$

preferably dimethyldimethoxysilane, dimethyldiethoxysilane, methylpropyldimethoxysilane or methylpropyldiethoxysilane, and/or mixtures of water-insoluble alkyltrialkoxysilanes and dialkyldialkoxysilanes of the general formulae II and III, where R is an amino-functional organic group,
$R^1$, $R^{1*}$, $R^{1}$ and $R^{1*}$ are a methyl or ethyl radical,
$R^2$ is a linear or cyclic or branched alkyl radical having 1 to 8 carbon atoms,
A is an unbranched or branched alkyl radical having 1 to 3 carbon atoms and
A' is an unbranched or branched alkyl radical having 1 to 3 carbon atoms, and
$0 \leq v \leq 1$, adding water to the mixture and adjusting the pH of the reaction mixture to between 1 and 8, and removing the alcohol which is already present and/or has been produced in the reaction.

The oligomeric silane system can also be prepared by mixing Q moles of water-soluble aminoalkylalkoxysilanes of the general formula I

$$R\!-\!Si(R^1)_v(OR^{1*})_{3-v} \qquad (I),$$

preferably aminopropyltriethoxysilane, aminopropylmethyldiethoxysilane, aminopropyltrimethoxysilane or aminopropylmethyldimethoxysilane, with M moles of water-insoluble alkylalkoxysilanes of the general formula IIb

$$R^3\!-\!Si(OR^{1**})_3 \qquad (IIb),$$

where R is an amino-functional organic group,
$R^1$, $R^{1*}$ and $R^{1**}$ are a methyl or ethyl radical and
$R^3$ is a linear or cyclic or branched alkyl radical having 1 to 6 carbon atoms or a ureido alkyl group of the general formula IV

$$NH_2\!-\!CO\!-\!NH\!-\!(CH_2)_b\!-\!, \text{ where } 1 \leq b \leq 6, \qquad (IV)$$

preferably b=3,
and
$0 \leq y \leq 1$, in the molar ratio $0<M/Q\leq 2$, adding water to the mixture, adjusting the pH of the reaction mixture to between 1 and 8, and removing the alcohol which is already present and/or has been produced in the reaction.

Furthermore, the oligomeric silane system is obtainable by mixing water-soluble organosilanes of the general formula V $$H_2N(CH_2)_f(NH)_g(CH_2)_f\!-\!Si(CH_3)_h(OR^0)_{3-h} \tag{V}$$

in which $0\leq f\leq 6$, $g=0$ if $f=0$, $g=1$ if $f>1$, $0\leq i\leq 6$, $0\leq h\leq 1$ and $R^0$ is a methyl, ethyl, propyl or isopropyl group, preferably aminopropyltriethoxysilane, with water-soluble organosilanes, which are nevertheless unstable in the aqueous medium, of the general formula VI

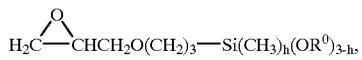

(VI)

in which $0\leq h\leq 1$ and $R^0$ is a methyl, ethyl, propyl or isopropyl radical, preferably glycidyloxypropyltrimethoxysilane, and/or of the general formula VII $$H_2C=CR'-COO(CH_2)_3-Si(CH_3)_h(OR^0)_{3-h} \tag{VII}$$

in which $0\leq h\leq 1$, $R^0$ is a methyl, ethyl, propyl or isopropyl radical and $R'$ is a methyl radical or hydrogen, preferably methacryloxypropyltrimethoxysilane, and a water-insoluble organosilane of the general formula VIII $$R''-Si(CH_3)_h(OR^0)_{3-h} \tag{VIII}$$

in which $0\leq h\leq 1$, $R^0$ is a methyl, ethyl, propyl or isopropyl radical and $R''$ is a linear, branched or cyclic hydrocarbon radical having 1 to 8 carbon atoms, preferably propyltrimethoxysilane, in the molar ratio $M=a/(b+c+d)$, where a is the sum of the mole fractions of the organosilanes according to formula V, b is the sum of the mole fractions of the organosilanes according to formula VI and c is the sum of the mole fractions of the organosilanes according to formula VII and d is the sum of the mole fractions of the organosilanes according to formula VIII, with $0\leq M\leq 3$, especially for M=0 with a=0 and/or c=d=0 and $b\geq 1$ and also, preferably $0.5\leq M\leq 3$, adding a water/acid mixture to the mixture, adjusting the pH of the reaction mixture to between 1 and 8, and removing the alcohol which is already present and/or has been produced in the reaction.

During the distillative removal of the alcohol it is preferred to add water at the rate at which alcohol or alcohol/water mixture is removed from the reaction medium. For adjusting the pH, monobasic acids are particularly suitable. Products prepared in this way do not liberate any further alcohols by hydrolysis, even on dilution with water, and have a flash point of distinctly more than 70° C.

An oligomeric silane system which can be prepared by the manner described above is, for example, VPHS 2927, an oligomeric silane system from Hüls AG which has the following composition and approximate structure:

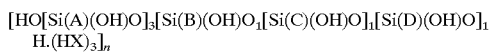

where
A=3-aminopropyl-
B=glycidyloxypropyl-
C=methacryloxypropyl-
D=propyl-
$n\geq 1$.

Furthermore, the object according to the present invention is achieved by a process for the preparation of a pearl lustre pigment based on a metal oxide-coated, platelet-form substrate and a top layer located on the metal oxide layer, in which the metal oxide-coated substrate is suspended in water, in a first step the corresponding oxide hydrates are precipitated, either simultaneously or in succession, at a temperature from 30 to 100° C., preferably from 40 to 75° C., by the addition of suitable formulations, for example aqueous salt solutions or organic metal compounds of at least two elements from the group consisting of silicon, aluminium, cerium and zirconium, the oxide hydrates of silicon and aluminium being precipitated at a pH of from 5 to 9 and the oxide hydrates of cerium and zirconium being precipitated at a pH of from 3 to 7 onto the substrate, and the pH is kept constant by simultaneous addition of acid or alkali or an appropriate buffer system, and in a second step at a pH of from 3 to 8 an oligomeric silane system is added which is bound on the pigment surface, and subsequently the pigment is separated off, washed with deionised water and dried at from 80 to 160° C., preferably from 120 to 160° C.

The invention relates, furthermore, to the use of the novel pigments for pigmenting coating materials, printing inks, plastics and cosmetics. For this purpose they can be employed in the form of mixtures with commercially available pigments, for example inorganic and organic absorption pigments, metal-effect pigments and LCP pigments.

The substrates used are pigments which consist of a platelet-form material, for example mica, kaoline or glass, and one or more metal oxide layers deposited thereon. The metal oxide layer may consist, for example, of titanium dioxide, iron(III) oxide, chromium oxide, zirconium dioxide, tin dioxide, zinc oxide or mixtures thereof. Pigments of this kind are commercially available under the designation Iriodin® (Manufacturer: Merck KGaA, Darmstadt).

The proportion of the total pigment made up by the top layer is from 1 to 20% by weight, preferably from 4 to 10% by weight. Of this, from 2 to 8% is made up by the metal oxides and from 2 to 12% by weight by the water-based oligomeric silane system.

The silanes or water-based oligomeric silane systems used are described in more detail in European Patent Applications Nos. 0 675 128, 0 716 127 and 0 716 128.

The resulting water-based oligomeric silane systems (organopolysiloxane-containing compositions on an aqueous basis) are essentially free from organic solvents and have a flash point of more than 70° C. Since by mixing with water the alkoxy groups have already substantially been hydrolysed, less than 5% by weight of alcohols (methanol, ethanol) are released by hydrolysis on dilution with water.

The result comprises, for example, compounds having the following approximate structure (formula IX)

Formula IX:

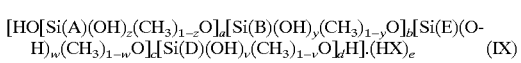

where
A=aminoalkyl radical derived from the general formula V,
B=glycidyl ether alkyl radical derived from the general formula VI,
E=acryloxyalkyl or methacryloxyalkyl radical of the general formula VII,
D=alkyl radical of the general formula VIII, HX=monobasic acid, where X=inorganic or organic acid radical such as, for example, chloride, nitrate, formate, acetate, v is equal to 0 or 1 and w is equal to 0 or 1 and y is equal to 0 or 1 and z is equal to 0 or 1 and a+b+c+d≧4 and a≦e≦2a, where 0≦a/(b+c+d)≦3, especially for a/(b+c+d) equal to 0 if a=0 and/or c equal to d equal to 0 and b≧1 and also for 0.5≦a/(b+c+d)≦3.

The job of the silicon-functional hydroxyl groups is to form chemical bonds to the hydroxyl groups of the pigment surface. This produces a stable bond between the silane and the pigment surface.

The job of the organofunctional groups of the oligomeric silane is to form bonds to the polymer of the waterborne coating system. Since the oligomers can be equipped with a plurality of functional groups differing from one another, the pigment can be used in different waterborne coating systems. Equipping it with methacrylic and amino groups means, for example, that the pigment can be employed for waterborne coating systems including polyester as polymer and for waterborne coating systems including polyurethane as polymer.

In a first embodiment, novel pigments are prepared by depositing from 0.1 to 10% by weight, preferably from 0.5 to 3% by weight, of silicon dioxide on the metal oxide layer of the substrate (base pigment) in a first step. To do this, a dilute solution of sodium silicate is metered into an aqueous suspension with a concentration of from 1 to 35%, preferably from 5 to 20%, of the base pigment in a pH range from 6 to 9. The pH is kept constant by adding hydrochloric acid, all pH values indicated being determined with the aid of a calibrated electrode.

In a second step, after the pH has been adjusted to a range from 3 to 5, aqueous salt solutions or solid salts of the metals cerium, aluminium or zirconium or mixtures thereof are added in a concentration of from 1 to 4% by weight, based on oxide, and in the presence of a soluble sulfate to an aqueous suspension of the substrate coated in step 1, the pH being kept constant in the range from 3 to 5 and the suspension being heated at from 30 to 100° C., preferably from 40 to 75° C., with stirring for from 5 minutes to 4 hours, preferably from 30 minutes to 2 hours.

Under these conditions only some—not more than 50%— of the metal ions are precipitated as hydroxides or oxide hydrates.

Then, in a third step, from 1 to 20% by weight, preferably from 2 to 12% by weight, of oligomeric silane system, based on the pigment employed, is added, the suspension is stirred at a pH of from 3 to 5 for from 5 minutes to 4 hours, preferably from 30 minutes to 2 hours, then the pH is adjusted over the course of from 5 minutes to 4 hours, preferably from 30 minutes to 2 hours, then the pH is adjusted over the course of from 5 minutes to 4 hours, preferably from 30 minutes to 2 hours, to a range from 5 to 8, the suspension being maintained at a temperature of from 30 to 100° C., preferably from 40 to 75° C.

Under these conditions, complete coprecipitation of the remaining metal ions as hydroxides or oxide hydrates takes place, together with the oligomeric silane system.

The pigment is subsequently separated off, washed salt-free and dried at from 80 to 180° C., preferably from 120 to 160° C.

In a second embodiment, the novel pigments are prepared by depositing, in a first step, from 0.1 to 10% by weight, preferably from 0.5 to 3% by weight (calculated on $Al_2O_3$) of aluminium oxide hydrate onto the metal oxide layer of the substrate. This is done by metering a dilute aluminium chloride solution into an aqueous suspension with a concentration of from 1 to 35%, preferably from 5 to 20%, of the basic pigment in the pH range from 7 to 9 and at a temperature from 40 to 80° C. over a period of two hours.

The pH is kept constant by simultaneous addition of sodium hydroxide solution.

Subsequently, in a second step carried out under the same conditions as for the precipitation of the aluminium oxide hydrate, silicon dioxide hydrate is precipitated onto the aluminium oxide hydrate layer in a quantity of from 0.1 to 10% by weight, preferably from 0.5 to 3% by weight, based on the base pigment, by adding a dilute sodium silicate solution. The pH is kept constant within the range from 7 to 9 by simultaneous addition of hydrochloric acid.

Then, in a third step, a from 20 to 60% aqueous solution of an oligomeric silane system is metered into the pigment suspension at from 40 to 80° C. over a period of from 10 minutes to 2 hours, preferably from 30 to 90 minutes. The amount metered in is from 2 to 12% by weight, based on the base pigment. The pigment is subsequently separated off from the reaction solution, washed salt-free and dried at from 80 to 180° C., preferably from 120 to 160° C.

In a further embodiment, the precipitation of aluminium oxide hydrate and silicon oxide hydrate onto the base pigment can also take place by hydrolysis of a silicon/ aluminium ester of the general formula X

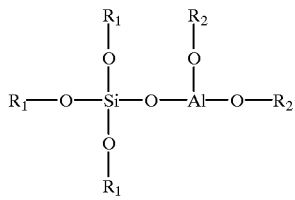

(X)

in which $R_1$ and $R_2$ can be identical or different and are an alkyl group having 1 to 8 carbon atoms. Preference is given to the use of a compound in which $R_1$ is an ethyl group and $R_2$ a secondary butyl group. This compound is marketed under the designation DYNASIL® Si—Al by Hüls Aktiengesellschaft, Marl.

The ethanolic solution of silicon/aluminium ester is metered into the suspension of the base pigment, heated at from 30 to 50° C., at a pH of from 4 to 9, preferably 5.5–7.5, over a period of from 10 minutes to 2 hours, preferably from 30 to 90 minutes. The oligomeric silane system is then added to the reaction mixture in the manner described.

In an additional embodiment, the oligomeric silane system can be replaced or supplemented by one or more monomeric silanes. These monomeric silanes can be an alkyltrialkoxysilane (especially methyltrimethoxysilane, methyltriethoxysilane, ethyltrimethoxysilane, ethyltriethoxysilane, propyltrimethoxysilane, propyltriethoxysilane, isobutyltrimethoxysilane, isobutyltriethoxysilane, octyltrimethoxysilane, octyltriethoxysilane) or a dialkyldialkoxysilane (especially dimethyldimethoxy—a glycidyloxyalkylalkoxysilane (especially glycidyloxypropyltrimethoxysilane, glycidyloxypropyltriethoxysilane, glycidyloxypropylmethyldimethoxysilane, glycidyloxypropylmethyldiethoxysilane) or a methacryloxyalkylalkoxysilane (especially methacryloxypropyltrimethoxysilane, methacryloxypropyltriethoxysilane, methacryloxypropylmethyldimethoxysilane, methacryloxypropylmethyldiethoxysilane) or a vinylalkoxysilane (especially vinyltrimethoxysilane, vinyltriethoxysilane, vinyltrimethoxyethoxysilane, vinylmethyldimethoxysilane, vinylmethyldiethoxysilane) or a mixture thereof.

In a third embodiment, the novel pigments are prepared by depositing, in a first step, from 0.1 to 5% by weight, preferably from 0.5 to 3% by weight, of cerium oxide hydrate onto the metal oxide layer of the substrate (base pigment). This is done by metering a dilute cerium chloride solution into an aqueous suspension of the base pigment with a concentration of from 1 to 35%, preferably from 5 to 20%, which is heated at from 40 to 80° C., over the course of 20 minutes within the pH range from 1 to 4, the pH being kept constant by adding sodium hydroxide solution.

In a second step under the same reaction conditions, a mixture of zirconium oxide chloride, sodium hypophosphite and hydrochloric acid is metered in over a period of from 10 minutes to 2 hours, preferably from 30 to 90 minutes, and zirconium oxide hydrate is precipitated onto the cerium oxide hydrate layer. The amount of zirconium oxide hydrate deposited is from about 0.1 to 10% by weight, preferably from 0.1 to 5% by weight of $ZrO_2$ based on the base pigment.

Since under the stated conditions the oxide hydrates of zirconium and cerium are not precipitated completely, in a third step the pH is raised to 9 by addition of sodium hydroxide solution over the course of hydrates of zirconium and cerium are not precipitated completely, in a third step the pH is raised to 9 by addition of sodium hydroxide solution over the course of 30 minutes, and the precipitation of the oxide hydrates is completed.

After subsequent stirring for 60 minutes, a from 20 to 60% aqueous solution of an oligomeric silane system is metered into the pigment suspension at a pH of from 7 to 9, at from 40 to 80° C. and over a period of one hour. The pigment is subsequently separated off from the reaction solution, washed salt-free and dried at from 80 to 180° C., preferably from 120 to 160° C.

The neutral-colour pigments obtained in this way have very good weathering resistance, which is demonstrated by the test results set out below. The pigment is on the one hand readily free-flowing and on the other hand possesses very good suitability for water-thinable coating systems, especially automotive paint systems, in respect of dispersibility, stability, colour properties, microbubble formation, swelling and lustre.

Through the modification of the pigment surface with different functional groups, the pigment can be employed for the various waterborne coating systems without the need for any special adaptation.

The novel pigments were tested in accordance with the following two test methods:

Water Immersion Test

The pigment samples were incorporated into a conventional paint system and the test samples were prepared by spray application. Testing was carried out in a one-coat system after 16 hours at 66° C. and after 20 hours at 80° C. During this time, the test samples are half-immersed in distilled water. The grey coloration was assessed visually after weathering in accordance with ISO 105 Part A 02 (by means of DIN 54 001) 24 hours after the end of exposure. The assessment scale extends from 5 (very good) to 1 (very poor).

Condensation Water Test

The pigment samples were incorporated into a waterborne coating system and the test samples were prepared by spray application.

The test was carried out in accordance with DIN 50 017 (condensation water/constant climate) 10 minutes to one hour after the end of exposure.

The assessment of the degree of bubble formation was made visually in accordance with DIN 53 209. "m" denotes frequency of bubbles per unit area, and "g" denotes the bubble size. The assessment scale extends from 0 (very good) to 5 (very poor), i.e. the reverse of the previous test method.

The swelling process was assessed visually in accordance with DIN 53 230, Table 2. In the relative assessment scale, the number 0 means "unchanged" and the number 5 means "fairly considerably changed".

Table 1 shows the test results for the pigments prepared in accordance with Examples 1 to 8, in accordance with the present invention, as measured by the test methods described above.

The zero sample shown at the end consisted of the pure waterborne coating systems without pigment. The zero sample shows that the pure waterborne coating systems also exhibit slight swelling.

The base pigments used, with the exception of Example 8, were purified prior to aftercoating. This was done by introducing them into water to form a 10% suspension, the water having been adjusted to a pH of from 10 to 11. The suspension was left overnight and the cloudy supernatant solution was decanted off.

TABLE 1

| Ex. No. | Base pigment used | | | Hydrosil VPHS 2909 employed* | Filtration time (min) | Yield (%) based on base pigment | Elemental analysis | | | Water immersion text (→ conv. coating system) | | Condensation water test (→ waterborne coating system) | | |
|---|---|---|---|---|---|---|---|---|---|---|---|---|---|---|
| | Type | Purification | Chemical structure | | | | C (%) | H (%) | N (%) | 16 h 66° C. | 20 h 80° C. | 1 | 2 | 3 |
| 1 | Ir. 103 | YES | $TiO_2$ low coat thickness | 3% | 120 | 102 | 1.0 | 0.2 | 0.1 | 5 | 5–4 | 1.0 | | |
| 2 | Ir. 215 | YES | $TiO_2$ medium coat thickness | 3% | 85 | 102 | 0.7 | 0.2 | not detectable | 5–4 | 4 | 1.0 | | |
| 3 | Ir. 235 | YES | $TiO_2$ high coat thickness | 3% | 75 | 101.8 | 0.6 | 0.2 | not detectable | 5 | 5–4 | 1.0 | | |
| 4 | Ir. 7235 | YES | $TiO_2$ very high coat thickness | 3% | 40 | 102.2 | 0.6 | 0.2 | not detectable | 5 | 5–4 | 1.0 | | |
| 5 | Ir. 444 | YES | $TiO_2 + Cr_2O_3$ mixed oxides | 3% | 50 | 101.9 | 0.6 | 0.2 | not detectable | 5 | 5–4 | 1.0 | | |
| 6 | Ir. 303 | YES | $TiO_2 + Fe_2O_3$ mixed oxides | 3% | 95 | 102.7 | 0.6 | 0.2 | not detectable | 5 | 5–4 | 1.0 | | |

TABLE 1-continued

| Ex. No. | Base pigment used Type | Base pigment used Purification | Base pigment used Chemical structure | Hydrosil VPHS 2909 employed* | Filtration time (min) | Yield (%) based on base pigment | Elemental analysis C (%) | Elemental analysis H (%) | Elemental analysis N (%) | Water immersion text (→ conv. coating system) 16 h 66° C. | Water immersion text (→ conv. coating system) 20 h 80° C. | Condensation water test (→ waterborne coating system) 1 | Condensation water test (→ waterborne coating system) 2 | Condensation water test (→ waterborne coating system) 3 |
|---|---|---|---|---|---|---|---|---|---|---|---|---|---|---|
| 7 | Ir. 504 | YES | $Fe_2O_3$ medium coat thickness | 3% | 160 | 102.9 | 0.6 | 0.2 | not detectable | 5 | 4–5 | 1.8 | | |
| 8 | Ir. 504 | NO | $Fe_2O_3$ medium coat thickness | 3% | 135 | 102.9 | 0.6 | 0.2 | not detectable | 5–4 | 4–5 | 1.8 | | |
| Zero sample | waterborne coating material | | | | | | | | | | | 1.3 | | |

*Hydrosil VPHS 2909: Designation of the oligomeric silane system employed in accordance with the invention, as from Example 5 of EP 0 716 127

Table 2 shows, for comparison, the test results for the conventional pigments used in Comparison Examples 1 to 6. The base pigment used was Iriodin® 9225 Rutil Perlblau, a mica pigment coated with titanium dioxide. In Comparison Examples 1 to 4 it was coated with an aftercoat comprising silicon dioxide, aluminium oxide, cerium oxide and one or more silanes according to U.S. Pat. No. 5,472,491. In Comparison Example 5 it was coated with zirconium oxide hydrate, cerium oxide hydrate and an epoxysilane according to EP 0 342 533. In Comparison Example 6 it was provided with an additional coating of chromium compounds and manganese compounds and two silanes having methacrylic groups and secondary amino groups, respectively.

A comparison of the test results after the condensation water test in both tables shows that the pigments in accordance with the present invention are of markedly greater stability in waterborne coating systems than the conventional pigments contained in Table 2. The only exceptions are the iron oxide pigments used in Examples 7 and 8. Their stability corresponds approximately to the pigments according to U.S. Pat. No. 5,472,491. These, however, have the advantage that they contain about 70% less silanes and can be used in various waterborne coating systems.

TABLE 2

| Comp. Ex. | Base pigment | Prior Art | Silanes used (and Zr/Al coupler) | Functionality | Filtration time (min) | Yield (%) based on base pigment | Assessment of the dried aftercoated pigment |
|---|---|---|---|---|---|---|---|
| 1 | Ir. 225 | US 5 472 491 Example 1 | 3% AMMO | prim. Amino | 90 | 101.7 | soft easily sieved |
| 2 | Ir. 225 | US 5 472 491 Example 2 | 3% AMMO +5% GLYMO +3% CPG | prim. amino + epoxy + carboxy | 95 | 102.8 | somewhat harder lumps easy to sieve |
| 3 | Ir. 225 | US 5 472 491 Example 2 | 3% AMMO +3% MEMO +3% GLYMO | prim. amino + methacrylic + epoxy | 85 | 104.4 | rel. hard lumps easy to sieve |
| 4 | Ir. 225 | US 5 472 491 Example 3 | 3% MEMO +5% GLYMO +3% CPG | methacrylic + epoxy + carboxy | 110 | 104.6 | rel. soft easy to sieve |
| 5 | Ir. 225 | EP 0 342 533 | 2% GLYMO | epoxy | | | soft easy to sieve |
| 6 | Ir. 225 | EP 0 104 516 | 0.2% MEMO +0.2% DAMO | methacrylic + sec. amino | | | soft easy to sieve |
| | zero sample | waterborne coating material 1 | | | | | |
| | zero sample | waterborne coating material 3 | | | | | |

| Comp. Ex. | Elemental analysis C (%) | Elemental analysis H (%) | Elemental analysis N (%) | Water immersion test (→ conv. coating system) 16 h 66° C. | Water immersion test (→ conv. coating system) 20 h 80° C. | Condensation water test (→ coating system) 1 | Condensation water test (→ coating system) 3 |
|---|---|---|---|---|---|---|---|
| 1 | 0.2 | 0.1 | not detectable | 5 | 4 | 2.0 | |
| 2 | 0.5 | 0.2 | not detectable | 4–5 | 3–4 | 1.9 | |
| 3 | 1.4 | 0.3 | 0.2 | 5 | 4–5 | 1.7 | |
| 4 | 1.0 | 0.3 | not detectable | 4–5 | 4–5 | 1.5 | |
| 5 | | | | | | 2.0 | 2.6 |
| 6 | | | | | | 2.5 | 2.3 |
| | | | | | | 1.1–1.3 | |
| | | | | | | 1.1 | |

Key to Table 2:
AMMO
3-Aminopropyltrimethoxysilane

TABLE 2-continued (DYNASYLAN ® AMMO)
Manufacturer: Hüls AG
GLYMO
3-Glycidyloxypropyltrimethoxysilane
(DYNASYLAN ® GLYMO)
Manufacturer: Hüls AG
MEMO
3-Methacryloxypropyltrimethoxysilane
(DYNASYLAN ® MEMO)
Manufacturer: Hüls AG
DAMO
N-Aminomethyl-3-aminopropyltrimethoxysilane
(DYNASYLAN ® DAMO)
Manufacturer: Hüls AG
CPG (Manchem ® C)
Carboxy-zirconium aluminate solution
Manufacturer: Rhône-Poulenc Chemicals The examples which follow are intended to illustrate the invention without limiting it.

EXAMPLE 1

200 g of Iriodin® 225 Rutil Perlblau (titanium dioxide-coated mica pigment from Merck KGaA, Darmstadt) are suspended in 1.8 l of deionized water and the suspension is heated with vigorous stirring to 40° C. The pH is adjusted to 10.5 with 5% sodium hydroxide solution. Generally, the pH is measured with a calibrated electrode.

Then a solution of 10.8 ml of sodium silicate (185 g $SiO_2$/l) in 300 ml of water is then added dropwise to the pigment suspension over the course of 30 minutes at a rate of 10 ml/min. During this time the pH is kept constant with 2.5% hydrochloric acid. After the end of the addition, the mixture is subsequently stirred at 40° C. for 15 minutes and then adjusted to a pH of 7.6 in the course of 20 minutes using 2.5% hydrochloric acid. Then 1.35 g of sodium sulfate, 2.30 g of aluminium and 1.10 g of cerium(III) chloride heptahydrate, all as solids, are added to the pigment suspension, the pH falling to 3.4.

The mixture is then heated to 75° C. over the course of 30 minutes, the pH falling to 2.9. The suspension is held at 75° C. with stirring for a further 75 minutes. During this time, at least part of the metal oxide hydrates are deposited.

Then 15 g of VPHS 2927, an oligomeric silane system from Hüls AG, Marl (see above), are added over the course of 10 minutes. The pH is kept constant at 2.8 by adding 2.5% hydrochloric acid. After the end of the addition, the mixture is subsequently stirred at 75° C. for 120 minutes. The pH is then adjusted to 8.5 over the course of 90 minutes by adding 2.5% sodium hydroxide solution. During this time, the metal oxide hydrates and the oligomeric silane system are deposited completely by coprecipitation on the pigment surface.

The mixture is subsequently stirred at 75° C. for after reaction for 60 minutes more, the pH falling to 8.0. After prolonged standing, the supernatant liquid is decanted off and the pigment is slurried with water, filtered off through a suction filter and dried at 140° C. for 16 hours.

EXAMPLE 2

200 g of Iriodin® 225 Rutil Perlblau (titanium dioxide-coated mica pigment from Merck KGaA, Darmstadt) are suspended in 1.8 l of deionized water and the suspension is heated with vigorous stirring to 75° C. The pH is adjusted to 8.0 with 2.5% hydrochloric acid.

Subsequently, a solution of 9.5 g of $AlCl_3.8\ H_2O$ in 100 ml of water is added dropwise over the course of 120 minutes at a rate of 0.9 ml/min, during which time the pH is kept constant by simultaneous addition of 2.5% sodium hydroxide solution.

Following subsequent stirring for 10 minutes, a solution of 16.2 ml of sodium silicate (185 g $SiO_2$/l) in 100 ml of water is metered in over the course of 120 minutes at a rate of 1.0 ml/min. After the end of the addition, stirring is continued for 10 minutes more. During the precipitation, the pH is kept at 8.0 by adding 2.5% sulfuric acid.

Then 15 g of VPHS 2927, an oligomeric silane system from Hüls AG, Marl (see above), are added over the course of 10 minutes. The pH is kept constant at 2.8 by adding 2.5% hydrochloric acid. After the end of the addition, stirring is continued at 75° C. for 120 minutes. Then the pH is adjusted to 8.5 over the course of 90 minutes by adding 2.5% sodium hydroxide solution. During this time, the oligomeric silane system is bonded completely on the pigment surface. Subsequently, stirring is continued at 75° C. for after reaction, for 60 minutes, during which the pH falls to 8.0.

After prolonged standing, the supernatant liquid is decanted off and the pigment is slurried with water, filtered off through a suction filter and dried at 140° C. for 16 hours.

EXAMPLE 3

200 g of Iriodin® 225 Rutil Perlblau (titanium dioxide-coated mica pigment from Merck KGaA, Darmstadt) are suspended in 1.8 l of deionized water and the suspension is heated with vigorous stirring to 75° C. The pH is adjusted to 2.5 with 5% hydrochloric acid.

Subsequently a solution of 2.20 g of $CeCl_3.7H_2O$ in 44 ml of water is added dropwise to the pigment suspension over the course of 20 minutes at a rate of 2.2 ml/min, the pH remaining constant at 2.5.

Then a solution of 11.52 g of $ZrOCl_2.8H_2O$, 7.58 g of $NaH_2PO_2.H_2O$ and 11.50 g of 37% hydrochloric acid in 668 ml of water is added over the course of 60 minutes at a metering rate of 11.3 ml/min and the pH is kept constant by simultaneous addition of 5% sodium hydroxide solution.

The solution is prepared by introducing the $ZrOCl_2$ solution at room temperature, as the initial charge, and metering in the $NaH_2PO_2$ solution with vigorous stirring over the course of 60 minutes at a rate of 6.3 ml/min. The concentrated hydrochloric acid is then added over the course of 1 minute, and after stirring for 10 minutes a clear solution is obtained. Following the addition of the mixture, stirring is continued at 75° C. for 30 minutes more.

Then 5% sodium hydroxide solution is metered in over the course of 35 minutes at a rate of 2.0 ml/min. The pH rises to 8.5, whereby complete precipitation of the oxide hydrates is achieved. Subsequently, 15 g of VPHS 2927, an oligomeric silane system from Hüls AG (see above) as a 40% aqueous solution are added over the course of 60 minutes at a rate of 1.9 ml/min. By simultaneous addition of NaOH, the pH is kept constant at 8.5. During this time, the oligomeric silane system is bound completely on the pigment surface. Subsequently, stirring is continued at 75° C. for after reaction for 60 minutes more, the pH falling to 8.0. After prolonged standing, the supernatant liquid is decanted off and the pigment is slurried with water, filtered off through a suction filter and dried at 140° C. for 16 hours.

EXAMPLE 4

200 g of Iriodin® 225 Rutil Perlblau (titanium dioxide-coated mica pigment from Merck KGaA, Darmstadt) are suspended in 1.8 l of deionized water and the suspension is heated with vigorous stirring to 40° C. The pH is adjusted to 6.5 using 2.5% hydrochloric acid. Then an ethanolic solution of the silicon/aluminium ester is metered in at a rate of 2.6 ml/min. Under these conditions, the ester is hydrolysed completely. The resulting aluminium oxide hydrate and silicon dioxide hydrate are precipitated onto the base pigment.

Subsequently, 15 g of VPHS 2927, an oligomeric silane system from Hüls AG (see above), are added to the reaction mixture, and the subsequent procedure is as in Example 3.

EXAMPLE 5

200 g of Iriodin® 225 Rutil Perlblau (titanium dioxide-coated mica pigment from Merck KGaA, Darmstadt) are suspended in 1.8 l of deionized water and the suspension is subsequently processed as in Example 4. However, instead of the oligomeric silane system propyltrimethoxysilane, a monomeric silane (manufacturer: Hüls AG), is metered in under the same conditions. The pigment is then worked up as in Example 3.

What is claimed is:

1. A modified pearl lustre pigment for waterborne coating systems, which comprises:
   a platelet-form substrate coated with at least one metal oxide,
   a top layer coating comprising at least two oxides and/or mixed oxides selected from the group consisting of silicon dioxide, aluminium oxide, cerium oxide, titanium oxide and zirconium oxide, and
   wherein the pigment is coupled with a water-based oligomeric silane coupling agent.

2. A pearl lustre pigment according to claim 1, wherein the water-based oligomeric silane coupling agent is essentially free from organic solvents, has a flash point of more than 70° C. and releases less than 5% by weight of alcohols by hydrolysis on dilution with water.

3. A pearl lustre pigment according to claim 1, wherein the oligomeric silane coupling agent is prepared by
   mixing at least one water-insoluble aminoalkylalkoxysilane of the formula I $$R\text{—}Si(R^1)_v(OR^{1*})_{3-v} \qquad (I),$$

with at least one water-insoluble alkyltrialkoxysilane of the formula IIa $$R^2\text{—}Si(OR^{1**})_3 \qquad (IIa),$$

and/or water-insoluble dialkyldialkoxydilane of the formula III $$AA'\text{—}Si(OR^{1***})_2 \qquad (III),$$

and/or a mixture of water-insoluble alkyltrialkoxysilanes and dialkyldialkoxysilanes of the formulae IIa and III, where R is an amino-functional organic group, $R^1$, $R^{1*}$, $R^{1}$ and $R^{1*}$ are a methyl or ethyl radical,
$R^2$ is a linear or cyclic or branched alkyl radical having 1 to 8 carbon atoms,
A is an unbranched or branched alkyl radical having 1 to 3 carbon atoms and
A' is an unbranched or branched alkyl radical having 1 to 3 carbon atoms, and
$0 \leq v \leq 1$.

adding water to the mixture to effect oligomerization,
adjusting the pH of the oligomerized mixture to between 1 and 8, and
removing alcohol which is already present and/or has been produced in the oligomerization.

4. A pearl lustre pigment according to claim 1, wherein the oligomeric silane coupling agent is prepared by
   mixing Q moles of at least one water-insoluble aminoalkylalkoxysilane of the formula I $$R\text{—}Si(R^1)_v(OR^{1*})_{3-v} \qquad (I),$$

with M moles of at least one water-soluble alkylalkoxysilane of the formula IIb $$R^3\text{—}Si(OR^{1**})_3 \qquad (IIb),$$

where R is an amino-functional organic group,
$R^1$, $R^{1*}$ and $R^{1**}$ are a methyl or ethyl radical and
$R^3$ is a linear or cyclic or branched alkyl radical having 1 to 6 carbon atoms or a ureido alkyl group of formula IV $$NH_2\text{—}CO\text{—}NH\text{—}(CH_2)_b\text{—}, \text{ where } 1 \leq b \leq 6, \qquad (IV)$$

and
$0 \leq v \leq 1$, in the molar ratio $0 < M/Q \leq 2$, adding water to the mixture to effect oligomerization,
adjusting the pH of the oligomerized mixture to between 1 and 8, and
removing alcohol which is already present and/or has been produced in the oligomerization.

5. A pearl lustre pigment according to claim 1, wherein the water-based oligomeric silane coupling agent is prepared by
   mixing at least one water-soluble organosilane of the formula V $$H_2N(CH_2)_f(NH)_g(CH_2)_i\text{—}Si(CH_3)_h(OR^0)_{3-h} \qquad (V),$$

in which $0 \leq f \leq 6$, g=0 if f=0, g=1 if f>1, $0 \leq i \leq 6$, $0 \leq h \leq 1$ and $R^0$ is a methyl, ethyl, propyl or isopropyl group,
with at least one water-soluble organosilane which is unstable in an aqueous medium, of the formula VI $$\underset{H_2C\overset{O}{\diagup\!\!\!\diagdown}CHCH_2O(CH_2)_3\text{—}Si(CH_3)_h(OR^0)_{3-h},}{} \qquad (VI)$$

in which $0 \leq h \leq 1$ and $R^0$ is a methyl, ethyl, propyl or isopropyl radical,
and/or of the formula VII $$H_2C\text{=}CR'\text{—}COO(CH_2)_3\text{—}Si(CH_3)_h(OR^0)_{3-h} \qquad (VII),$$

in which $0 \leq h \leq 1$, $R^0$ is a methyl, ethyl, propyl or isopropyl radical and R' is a methyl radical or hydrogen,
and at least one water-insoluble organosilane of the formula VIII $$R''\text{—}Si(CH_3)_h(OR^0)_{3-h} \qquad (VIII),$$

in which $0 \leq h \leq 1$, $R^o$ is a methyl, ethyl, propyl or isopropyl radical and R" is a linear, branched or cyclic hydrocarbon radical having 1 to 8 carbon atoms, in the molar ratio M=a/(b+c+d), where a is the sum of the mole fractions of the organosilanes according to formula V, b is the sum of the mole fractions of the organosilanes according to formula VI, c is the sum of the mole fractions of the organosilanes according to formula VII and d is the sum of the mole fractions of the organosilanes according to formula VIII, with $0 \leq M \leq 3$, and adding a water/acid mixture to the mixture to effect oligomerization, adjusting the pH of the oligomerized mixture to between 1 and 8, and removing alcohol which is already present and/or has been produced in the oligomerization.

6. A pearl lustre pigment according to claim 1, wherein the proportion of the total pigment made up by the top layer is from 1 to 20% by weight.

7. A pearl lustre pigment according to claim 1, wherein the oligomeric silane coupling agent is of the formula (IX):

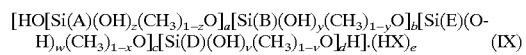

wherein,

A is an aminoalkyl radical,

B is glycidyl ether alkyl radical,

E is an acryloxyalkyl or methacryloxy radical,

D is an alkyl radical,

HX is a monobasic acid, v, w, y and z are each equal to 0 or 1, and letters a to e are numbers satisfying the relationships: $a+b+c+d \geq 4$, $a \leq e \leq 2a$ and $0 \leq a/(b+c+d) \leq 3$.

8. A coating printing ink, plastic, cosmetic or coating material composition which comprises a modified pearl luster pigment according to claim 1.

9. A process for preparing a pearl lustre pigment for waterborne coating systems, wherein the pigment comprises:

a platelet-form substrate coated with at least one metal oxide, a top layer coating comprising at least two oxides and/or mixed oxides selected from the group consisting of silicon dioxide, aluminium oxide, cerium oxide, titanium oxide and zirconium oxide, and wherein the pigment is coupled with a water-based oligomeric silane coupling agent, which process comprises:

suspending the platelet-form substrate coated with at least one metal oxide in water, precipitating corresponding oxide hydrates of the at least two oxides and/or mixed oxides selected from the group consisting of silicon dioxide, aluminium oxide, cerium oxide, titanium oxide and zirconium oxide, either simultaneously or in succession as a top layer on the pigment at a temperature of from 30 to 100° C., adding the oligomeric silane coupling agent at a pH of 3 to 8 so that it is coupled to said top layer on the pigment, and subsequently, separating the resulting pigment, washing with deionised water and drying at a temperature from 80 to 160° C.

10. The process of claim 9, wherein the precipitating of the corresponding oxide hydrates of the at least two oxides and/or mixed oxides as a top layer on the pigment is conducted at a temperature of from 40 to 75° C.

11. The process of claim 9, wherein the precipitating of the corresponding oxide hydrates of the at least two oxides and/or mixed oxides as a top layer on the pigment is conducted at a pH of 5 to 9 when the oxide hydrates are of silicon dioxide or aluminium oxide, and at a pH of 3 to 7 when the oxide hydrates are of cerium oxide, titanium oxide or zirconium oxide.

12. The process according to claim 9, wherein the corresponding oxide hydrates of at least two oxides and/or mixed oxides are precipitated as a top layer from an organometallic compound which is an ester of the formula X

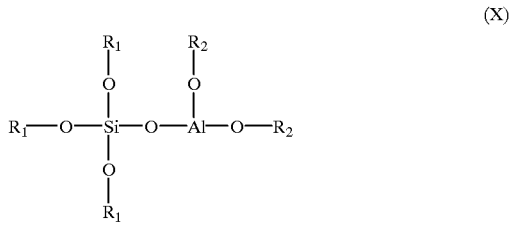

in which $R_1$ and $R_2$ are identical or different and are an alkyl group having 1 to 8 carbon atoms.

13. The process of claim 9, wherein a monomeric silane is used as a coupling agent in addition to the oligomeric silane coupling agent.

14. The process according to claim 13, wherein the monomeric silane is an alkyltrialkoxysilane, a dialkyldialkoxysilane, a glycidyloxyalkylalkoxysilane, a methacryloxyalkylalkoxysilane, a vinylalkoxysilane or a mixture thereof.

* * * * *